(12) United States Patent
van Barneveld et al.

(10) Patent No.: US 6,489,519 B1
(45) Date of Patent: Dec. 3, 2002

(54) PROCESS FOR REMOVAL OF IMPURITIES FROM PHENOL BY MEANS OF AT LEAST ONE ACID CATALYST

(75) Inventors: Heinrich van Barneveld, Bottrop (DE); Otto Gerlich, Gladbeck (DE); Wilfried Jordan, Dorsten (DE); Otto Schnurr, Kapellen (DE); Hugo H. J. M. Liefooche, Edegem (DE)

(73) Assignee: Phenolchemie GmbH & Co. KG, Gladbeck (DE)

( * ) Notice: Subject to any disclaimer, the term of this patent is extended or adjusted under 35 U.S.C. 154(b) by 0 days.

(21) Appl. No.: 09/696,205

(22) Filed: Oct. 26, 2000

(30) Foreign Application Priority Data

Oct. 26, 1999 (DE) .......................................... 199 51 373

(51) Int. Cl.$^7$ .............................................. C07C 37/68
(52) U.S. Cl. ....................................... 568/754; 568/749
(58) Field of Search .................................. 568/754, 749

(56) References Cited

U.S. PATENT DOCUMENTS

| | | | | |
|---|---|---|---|---|
| 3,029,292 A | * | 4/1962 | Nixon | |
| 3,029,293 A | * | 4/1962 | Nixon | |
| 3,029,294 A | * | 4/1962 | Keeble | |
| 3,810,946 A | * | 5/1974 | Yeh | |
| 4,634,796 A | * | 1/1987 | Suciu | |
| 5,131,984 A | * | 7/1992 | Chan | |
| 5,414,154 A | * | 5/1995 | Jenczewski | |
| 6,066,767 A | * | 5/2000 | Zakoshansky | |

FOREIGN PATENT DOCUMENTS

| | | |
|---|---|---|
| EP | 1 018 501 | 7/2000 |
| FR | 1 302 848 | 7/1962 |
| GB | 1108584 | * 4/1968 |

* cited by examiner

*Primary Examiner*—Michael L. Shippen
(74) *Attorney, Agent, or Firm*—Oblon, Spivak, McClelland, Maier & Neustadt, P.C.

(57) ABSTRACT

Impurities are removed from phenol by a process, comprising:
  first treating phenols containing impurities with at least one acid catalyst which converts the impurities into compounds which can be separated from phenol;
  separating the acid treated phenol from the compounds; and
  treating the distilled phenol a second time with at least one acid catalyst; thereby effectively removing the impurities from phenol.

22 Claims, 1 Drawing Sheet

PROCESS FOR REMOVAL OF IMPURITIES FROM PHENOL BY MEANS OF AT LEAST ONE ACID CATALYST

BACKGROUND OF THE INVENTION

1. Field of the Invention

The present invention relates to a process for removal of impurities from phenol by means of at least one acid catalyst.

2. Description of the Background

The synthesis of phenol by decomposition of cumene hydroperoxide is known. The reaction mixture obtained during decomposition is generally subjected to fractional distillation after it has been neutralized. During this distillation acetone is removed by distillation as the first main product. Thereafter, as the distillation is continued, the remaining isopropylbenzene, α-methylstyrene and water are also obtained in other fractions. Thereafter, crude phenol is removed by distillation in an overhead as the second main product, while a mixture of phenol, acetophenone, dimethylphenylcarbinol and p-cumylphenol together with numerous condensation and polymerization products remain in the bottoms of the distillation column. This crude phenol still contains impurities, which makes difficult or severely interferes with further processing of the phenol to derivative products. These impurities are, in particular, ketones, such as mesityl oxide, isomesityl oxide, methyl isobutyl ketone, hydroxyacetone and acetophenone, unsaturated compounds and/or methylbenzofuran. These compounds cannot be completely removed from the phenol by distillation.

German Patent No. 1668952 describes a process for preparing pure phenols which are almost free of mesityl oxide from crude phenols which form during decomposition of hydroperoxides of alkylaromatic hydrocarbons in the presence of acids followed by fractionation of the reaction mixture, by passage over stationary-bed catalysts of macroreticular ion exchangers containing active sulfonic acid groups or similar active acid groups at temperatures ranging from 45 to 200° C. and subsequent distillation. In this process the treatment of the crude phenols in liquid or vapor phase is accomplished without admixture of water. If necessary the reaction mixture is neutralized before distillation is performed. By means of this process weakly reactive carbonyl compounds such as methyl isobutyl ketone and methylcyclopentenone, as well as compounds such as 2-methylbenzofuran cannot be removed from the crude phenol at all, or can only be removed incompletely. The presumed reason for this is that equilibrium is established between the substances being withdrawn and the reaction products, and that further reaction of the reaction products is prevented by water formed during the reaction.

U.S. Pat. No. 5,414,154 teaches a process for reducing methylbenzofuran impurities in phenol obtained from the decomposition of cumene hydroperoxide. In this process the crude phenol is treated in such a way that it has an acetol content of less than 260 ppm. The crude phenol treated in this manner is contacted with an acid catalyst, whereby methylbenzofuran is converted to higher-boiling compounds, which are removed from the crude phenol by distillation. Implementation of this process is limited to the use of crude phenol having an acetol content of less than 260 ppm. A need continues to exist for removing impurities from phenol produced by the decomposition of cumene hydroperoxide.

SUMMARY OF THE INVENTION

Accordingly, one object of the present invention is to provide a process for the removal of impurities from phenol, which process, largely regardless of the composition of the impurities, is capable of separating phenol from impurities in a manner which is simple and uses the least possible amount of energy.

Briefly, this object and other objects of the present invention as hereinafter will become more readily apparent can be attained by a process of removing impurities from phenol comprising: first treating phenols containing impurities with at least one acid catalyst which converts the impurities into compounds which can be separated from phenol, separating the acid treated phenol from said compounds; and treating the separated phenol a second time with at least one acid catalyst, thereby effectively removing reactive impurities from phenol. The composition of the impurities has very little influence on the efficiency of the process.

Another aspect of the invention is a process of synthesizing phenol by removing impurities therefrom by the procedure set forth above.

BRIEF DESCRIPTION OF THE DRAWINGS

A more complete appreciation of the invention and many of the attendant advantages thereof will be readily obtained as the same becomes better understood by reference to the following detailed description when considered in connection with the accompanying drawings, wherein.

DETAILED DESCRIPTION OF THE PREFERRED EMBODIMENTS

Figure 1:
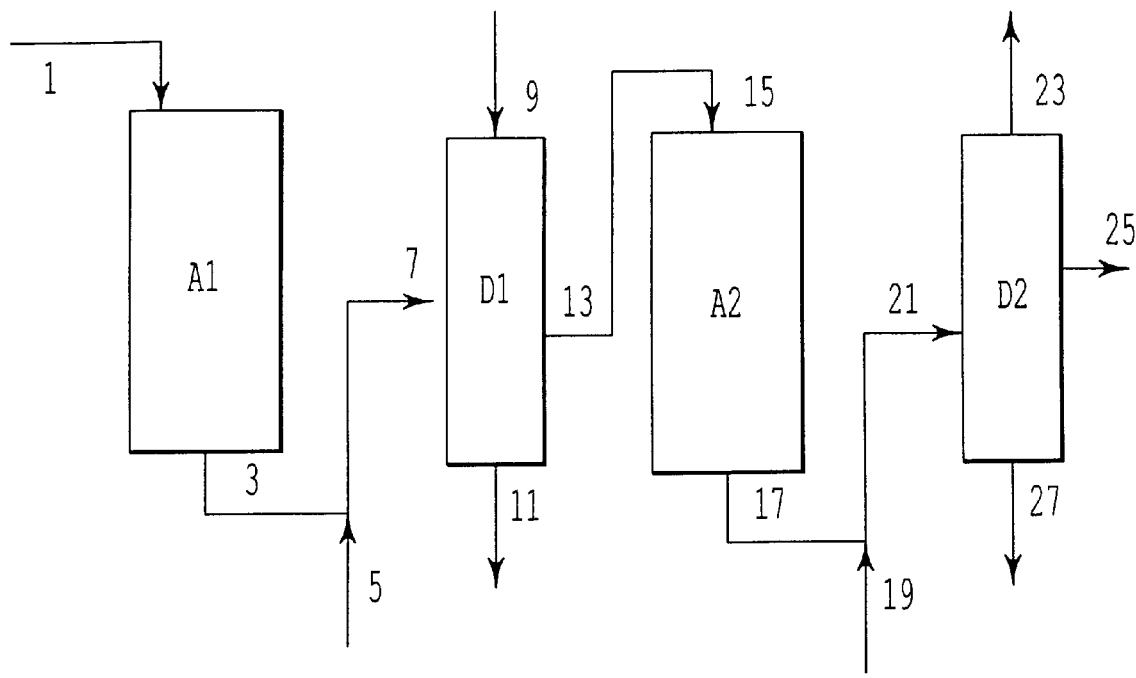
FIG. 1 is a flow diagram of an apparatus employed in the process of the invention.

The present invention is, therefore, a process of removing impurities from phenol by converting these impurities by means of at least one acid catalyst to compounds which can be separated from phenol. The compounds obtained from the impurities by acid conversion are separated from the phenol. The phenol is treated at least one additional time with an acid catalyst.

An aspect of the present invention is a process of synthesizing phenol in which the removal of impurities from phenol is accomplished by converting these impurities by means of at least one acid catalyst to compounds which can be separated from phenol. The compounds obtained from the impurities by acid conversion are thermally separated from the phenol. The phenol is treated at least one additional time with an acid catalyst.

The advantage of the present process is that, for removal of impurities having the usual composition from phenol obtained from the acid-catalyzed decomposition of cumene hydroperoxide and subsequent working-up of the decomposition products by distillation, it is not necessary to satisfy any limit values with respect to a particular constituent of the impurities.

In contrast to conventional processes, the removal of impurities is accomplished by two-stage treatment of the phenol with an acid catalyst, wherein treatment by distillation follows each treatment. Even though the process has one more distillation step than the conventional process, the energy consumption can be kept low by recycling the thermal energy employed.

By implementation of the present process for the removal of impurities from phenol by means of at least one acid catalyst, it is possible to purify phenol from diverse sources. The phenol can be produced in processes which are performed for synthesis or phenol or in processes in which phenol is used as a raw material. Preferably the phenol is a so-called crude phenol, which is obtained in the thermal work-up of phenol-containing streams. The present process can also be applied to pure phenol streams which are not sufficiently clean. Most preferably the crude phenol is obtained from thermal work-up of the decomposition product phase formed during acid-catalyzed decomposition of cumene hydroperoxide.

In the thermal work-up of phenol-containing phases, which is usually accomplished by distillation or rectification, phenol fractions are obtained which contain not only phenol, but also impurities that cannot be separated from phenol at all by thermal methods, or can be separated only incompletely in such a way. Examples of such impurities include mesityl oxide, isomesityl oxide, methyl isobutyl ketone, hydroxyacetone, acetophenone, methylcyclopentenone, methylstyrene, phenylketones and methylbenzofuran.

According to the invention, phenol fractions comprising phenol which contains impurities are treated with an acid catalyst. The acid catalyst can be, for example, an acid ion-exchange resin or a superacid catalyst. Any commercial ion-exchange resin can be used as the acid ion-exchange resin. Such ion-exchange resins contain, for example, aromatic sulfonic acid groups cross-linked with polystyrene. An example of such an ion-exchange resin is Amberlyst 15, which is available from Rohm and Haas.

As superacid catalysts, all catalysts which have an acid strength greater than that of 100% sulfuric acid can be used. Examples of such catalysts include $AlCl_3$, $SbF_5$ and sulfate groups immobilized on salts or oxides. Examples of catalysts which exhibit similar properties and thus can also be used in the present process are heteropoly acids of metal oxides of metals such as molybdenum or tungsten.

The treatment of the phenol fraction is preferably accomplished with an ion exchanger in a stationary-bed or fluidized-bed reactor, preferably with an ion exchanger in a stationary-bed reactor. Depending on the thermal stability of the catalyst, the treatment of the phenol fraction is performed at a temperature ranging from 100 to 200° C. or, if ion exchangers are used, preferably at a temperature of 100 to 130° C. After the treatment, in which part of the impurities has been converted to other compounds by various acid-catalyzed reactions, these impurities, as well as any water formed during these reactions, are largely separated from phenol. Separation can be accomplished mechanically and/or thermally. Mechanical separation can be used, for example, when the compounds present as impurities in the phenol have been converted by means of the acid catalyst into compounds that can be separated from one another by phase separation, filtration or similar methods for separation of compounds present in liquid/liquid, liquid/solid or liquid/gaseous phases. Examples of thermal separation methods include flash evaporation, distillation or rectification, as well as fractional crystallization or freezing-out of compounds. Preferably separation is accomplished by a thermal treatment in a distillation or rectification apparatus, preferably in a distillation column, wherein compounds with lower boiling point than phenol are largely removed by distillation as column overheads and compounds with higher boiling point than phenol remain in the column as bottoms. The phenol separated from the impurities is preferably removed from the column via a sidestream outlet.

The phenol obtained by thermal treatment, or the phenol separated by some other method of separation from compounds formed by the treatment with an acid catalyst, is brought to a temperature below 100° C. If separation is accomplished by a thermal treatment, the phenol is cooled to a temperature below 100° C. Cooling of the phenol can be accomplished, for example, in a heat exchanger, in which the thermally treated phenol transfers heat to the phenol yet to be treated with the catalyst. In this way part of the thermal energy needed for the thermal treatment can be recovered.

After the phenol which has been largely separated from the compounds formed from the impurities during the treatment with an acid catalyst, as well as from water of reaction, has been brought to a temperature below 100° C., it is treated once again with an acid catalyst. The treatment can also be performed in an ion exchanger, a stationary-bed reactor or a fluidized-bed reactor. Preferably the treatment is also repeated once again in an ion exchanger or a stationary-bed reactor. Suitable acid catalysts which can again be used include acid ion-exchange resin and/or a superacid catalyst as described hereinabove. This second treatment of the phenol is accomplished preferably at a temperature below 100° C., most preferably at a temperature of 75 to 95° C.

The phenol treated for the second time with at least one acid catalyst is again fed to mechanical and/or thermal separation, in which compounds formed from the impurities present in the phenol by reaction on at least one acid catalyst are again separated from the phenol. The separation can be performed in apparatuses such as described hereinabove. Once again a particularly preferred alternative is thermal separation. By performing thermal separation, the low-boiling compounds, high-boiling compounds and any water of reaction formed are once again separated from the phenol. By means of the separation process, especially thermal separation, there is obtained a phenol fraction which is very largely free of the impurities and can be sent to further processing.

It may be advantageous if the pH of the phenol fraction to be treated is increased by addition of a base before at least one of the inventive mechanical and/or thermal separations. Preferably the pH of the phenol is increased before thermal separation by addition of an alkali metal hydroxide, and especially preferably by addition of sodium hydroxide, in order to prevent reverse decomposition reactions during thermal separation.

In performing the present process it may be advantageous to conduct the thermal separation in distillation columns which permit part of the overhead product and/or part of the bottoms product to return to the column as reflux.

It may be advantageous to undertake mechanical separation first and then thermal separation. This procedure can be practical, for example, if phase separation takes place between phenol and at least part of the compounds formed by conversion of the impurities on at least one acid catalyst. In such a case it is advantageous first of all to separate the phases from one another, for example with a phase separator, and then to undertake thermal separation. By the combination of mechanical and thermal separation it is possible to reduce the quantity of energy needed for thermal separation, since the volume or total quantity that must be heated (distillation) or cooled (freezing-out) is smaller.

The present process can be performed batchwise or continuously. Preferably the present process is performed continuously.

The inventive process can be applied to all phenol streams which contain impurities. In particular, the present process can be applied to phenol streams produced in phenol-synthesis processes such as the Hock process, in order to remove impurities from phenol by means of an acid catalyst. Most preferably the present process is applied to phenol streams prepared by work-up by distillation of decomposition product formed in the acid-catalyzed decomposition of cumene hydroperoxide.

Figure 2:
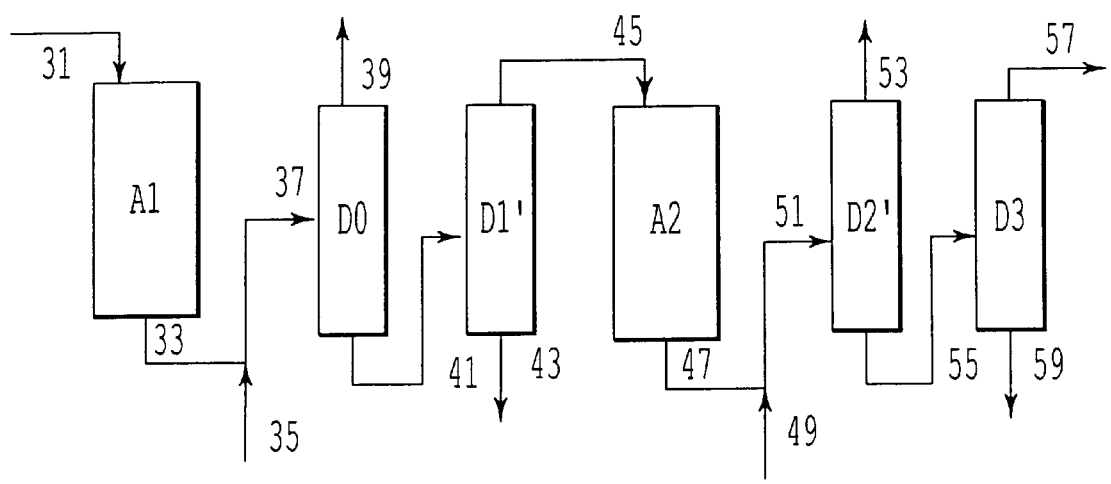
FIG. 2 is a flow diagram of another apparatus employed in the process of the invention.

FIGS. 1 and 2 illustrate possible embodiments of the present process, although the process is not to be construed as limited to such embodiments.

FIG. 1 illustrates one possible embodiment of the present process. In this embodiment the phenol which contains impurities is passed via a line 1 into an ion exchanger A1, which contains an acid catalyst. The phenol treated with at least one acid catalyst is passed by line 3 to the distillation column. A base can be mixed in with the phenol via line 5 before it enters distillation column D1 via line 7. At the head of distillation column D1, low-boiling compounds having a boiling temperature less than that of phenol can be removed via line 9. From the column bottoms high-boiling components having a boiling temperature higher than that of phenol can be removed via line 11. The phenol fraction largely freed of high-boiling and low-boiling compounds exits unit D1 at sidestream outlet 13 and passes via line 15 into a second ion exchanger A2. The phenol fraction treated with at least one acid catalyst exits ion exchanger A2 via line 17. A base can again be mixed in with this phenol fraction via line 19 before the phenol fraction is passed via line 21 into a second distillation column D2. From this distillation column D2, in which phenol is again removed by separation from high-boiling and low-boiling compounds, the low-boiling compounds can be removed overhead and sent to processing via line 23 and the high-boiling compounds can be removed from the column bottoms and sent to work-up via line 27. From the sidestream outlet, via line 25, a phenol fraction very largely freed of impurities can be withdrawn from the distillation column and sent to further work-up or processing.

FIG. 2 shows an alternative embodiment of the inventive process. In this embodiment the phenol which contains impurities is passed via line 31 into an ion exchanger A1, which contains an acid catalyst. The phenol treated with at least one acid catalyst is passed via line 33 to the distillation column D0. A base is mixed into the phenol via line 35 before it enters distillation column Do via line 37. At the head of distillation column Do low-boiling compounds with a boiling temperature lower than phenol can be removed via line 39. From the column bottoms a stream containing high-boiling compounds and phenol can be passed via line 41 into distillation column D1'. In distillation column D1' the high-boiling compounds are separated from the phenol. High-boiling compounds, which have a boiling temperature higher than that of phenol, can be removed from the column bottoms via line 43. The phenol fraction largely freed of high-boiling and low-boiling compounds is passed from the head of distillation column D1' via line 45 into a second ion exchanger A2. The phenol fraction treated with at least one acid catalyst exits ion exchanger A2 via line 47. A base can again be mixed in with this phenol fraction via line 49 before the phenol fraction is passed via line 51 into a further distillation column D2'. In distillation column D2' low-boiling compounds are separated. The low-boiling compounds can be removed overhead via line 53. A stream which contains the high-boiling compounds and the phenol is removed from the column bottom via line 55 and injected laterally into distillation column D3. From this column a phenol fraction very largely freed of impurities can be withdrawn overhead from the distillation column via line 57, and the fraction can be sent to further work-up or processing.

At the bottom of distillation column D3, a high-boiling fraction, or in other words compounds with a boiling point above that of phenol, can be removed and sent to further processing via line 59.

Having now generally described this invention, a further understanding can be obtained by reference to certain specific examples which are provided herein for purposes of illustration only and are not intended to be limiting unless otherwise specified.

EXAMPLES

Example: Removal of Impurities from Phenol

A phenol stream containing as impurities 300 ppm by weight mesityl oxide, 3000 ppm by weight hydroxy acetone and 450 ppm by weight methylbenzofuran among others was brought to a temperature of 115° C. in a heat exchanger. The phenol stream was passed over a stationary-bed ion exchanger, which was filled with Amberlyst 15 ion-exchange resin. The dwell time of the phenol stream in the ion exchanger was 4 hours. To the phenol stream treated in this ion exchanger there was added sufficient sodium hydroxide so that the pH of the phenol stream was about 7. The phenol stream treated in this way was transferred to a distillation column, in which the phenol stream was thermally treated. The temperature zone in the distillation column were selected such that a phenol fraction could be withdrawn at the sidestream outlet of the column, while predominantly compounds having a boiling temperature lower than that of phenol could be removed overhead and compounds having a boiling temperature higher than that of phenol could be removed at the column bottom. Analysis of the phenol fraction obtained from the sidestream outlet revealed the following contents: mesityl oxide<10 ppm by weight, hydroxy acetone<30 ppm by weight and methylbenzofuran<1000 ppm by weight.

This phenol fraction was cooled to a temperature of 85° C. in a heat exchanger, wherein the heat removed was used to heat phenol to be thermally treated. The phenol fraction prepared in this way was passed through a stationary-bed ion exchanger, which was filled with Amberlyst 15 ion-exchange resin. The dwell time of this phenol stream in the ion exchanger was 2.5 hours. To this phenol reaction treated with an acid catalyst there was again added sufficient sodium hydroxide so that the pH of the phenol fraction was about 7. The phenol fraction was heated via a heat exchanger and transferred to a further distillation column. Once again the temperature zone in the distillation column was adjusted such that a phenol fraction could be withdrawn at the sidestream outlet of the column, while predominantly compounds with a boiling temperature lower than that of phenol could be removed overhead and compounds with a boiling temperature higher than that of phenol could be removed at the column bottom. Analysis of the phenol fraction obtained from the sidestream outlet revealed the following contents: mesityl oxide<1 ppm by weight, hydroxy acetone<1 ppm by weight and methylbenzofuran<10 ppm by weight. On the basis of the results of analysis, it can be recognized very clearly that the contents of impurities in the phenol are much smaller because of the two-stage treatment with an acid catalyst than is the case in the conventional process, in which the treatment is performed only once with an acid catalyst.

The disclosure of German priority Application No. 19951373.2 filed Oct. 26, 1999 is hereby incorporated by reference into the present application.

Obviously, numerous modifications and variations of the present invention are possible in light of the above teachings. It is, therefore, to be understood that within the scope of the appended claims, the invention may be practiced otherwise than as specifically described herein.

What is claimed as new and is intended to be secured by Letters Patent is:

1. A process of removing impurities from phenol, comprising:

first treating crude phenols containing impurities obtained from the thermal work-up of phenol-containing streams with at least one acid catalyst which converts the impurities into compounds which can be separated from phenol;

separating the acid treated phenol from said compounds; and treating the separated phenol a second time with at least one acid catalyst; thereby effectively removing said impurities from phenol.

2. The process according to claim 1, wherein after the first treatment of the phenol with at least one acid catalyst, the phenol is separated mechanically or thermally from the compounds formed from the impurities.

3. The process according to claim 1, wherein the phenol treated a second time with acid catalyst is separated thermally from phenol by distillation a second time to produce a purified phenol product.

4. The process according to claim 1, wherein the acid catalyst is a superacid catalyst or an acid on-exchange resin.

5. The process according to claim 1, wherein the first treatment of the phenol with an acid catalyst is performed at a temperature of 100 to 1300° C.

6. The process according to claim 5, wherein the second treatment of the phenol with an acid catalyst is performed at a temperature of less than 1300° C.

7. The process according to claim 1, wherein the phenol is separated thermally from the compounds formed from impurities by rectification or distillation.

8. The process according to claim 7, wherein before thermal separation of the phenol, a base is added to the phenol which has been treated with at least one acid catalyst.

9. The process according to claim 8, wherein said base is sodium hydroxide.

10. The process according to claim 1, wherein the compounds formed by acid treatment with said impurities have a boiling temperature lower than, higher than or both of the phenol, as separation of these compounds from the phenol is accomplished thermally.

11. The process according to claim 2, wherein the thermal energy from the separation of phenol from impurities is recycled in the system for other thermal separation operations.

12. A process for the synthesis of phenol by removing impurities from phenol, comprising:

first treating crude phenols containing impurities obtained from the thermal work-up of phenol-containing streams with at least one acid catalyst which converts the impurities into compounds which can be separated from phenol;

thermally separating the acid treated phenol from said compounds; and treating the thermally separated phenol a second time with at least one acid catalyst; thereby effectively removing reactive impurities from phenol.

13. The process according to claim 12, wherein, after the first treatment of the phenol with at least one acid catalyst, the phenol is separated mechanically or thermally from the compounds formed from the impurities.

14. The process according to claim 12, wherein the phenol treated a second time with acid catalyst is separated thermally from phenol by distillation a second time to produce a purified phenol product.

15. The process according to claim 12, wherein the acid catalyst is a superacid catalyst or an ion-exchange resin.

16. The process according to claim 12, wherein the first treatment of the phenol with an acid catalyst is performed at a temperature of 100 to 130° C.

17. The process according to claim 16, wherein the second treatment of the phenol with an acid catalyst is performed at a temperature of less than 100° C.

18. The process according to claim 12, wherein the phenol is separated thermally from the compounds formed from impurities by rectification or distillation.

19. The process according to claim 18, wherein before thermal separation of the phenol, a base is added to the phenol which has been treated with at least one acid.

20. The process according to claim 19, wherein said base is sodium hydroxide.

21. The process according to claim 12, wherein the compounds formed by acid treatment with said impurities have a boiling temperature lower than, higher than or both of the phenol, as separation of these compounds from the phenol is accomplished thermally.

22. The process according to claim 13, wherein the thermal energy from the separation of phenol from impurities is recycled in the system for other thermal separation operations.

* * * * *

UNITED STATES PATENT AND TRADEMARK OFFICE
CERTIFICATE OF CORRECTION

PATENT NO. : 6,489,519 B1
DATED : December 3, 2002
INVENTOR(S) : Heinrich Van Barneveld et al.

It is certified that error appears in the above-identified patent and that said Letters Patent is hereby corrected as shown below:

Column 7,
Line 30, "1300º" should read -- 130º --.
Line 33, "1300º" should read -- 100º --.

Signed and Sealed this

Seventeenth Day of June, 2003

JAMES E. ROGAN
*Director of the United States Patent and Trademark Office*

UNITED STATES PATENT AND TRADEMARK OFFICE
CERTIFICATE OF CORRECTION

PATENT NO.   : 6,489,519 B1
DATED        : December 3, 2002
INVENTOR(S)  : Heinrich van Barneveld et al.

It is certified that error appears in the above-identified patent and that said Letters Patent is hereby corrected as shown below:

<u>Title page,</u>
Item [75], Inventors: "Kapellen (DE); Hugo H. J. M" should read -- Kapellen (BE); Hugo H. J. M. -- and "Liefooche, Edegem (DE)" should read -- Liefooghe, Edegem (BE) --.

<u>Column 7,</u>
Line 26, "acid on-exchange" should read -- acid ion-exchange --.

<u>Column 8,</u>
Line 24, "an ion-exchange" should read -- acid ion-exchange --.

Signed and Sealed this

Ninth Day of September, 2003

JAMES E. ROGAN
*Director of the United States Patent and Trademark Office*